United States Patent
Ikeda et al.

(10) Patent No.: US 7,202,060 B2
(45) Date of Patent: Apr. 10, 2007

(54) PROCESS FOR PRODUCING L-AMINO ACIDS VIA FERMENTATION METHOD

(75) Inventors: Masato Ikeda, Tokyo (JP); Makoto Yagasaki, Tokyo (JP); Yayoi Abe, Hofu (JP); Jun-ichi Takano, Cape Gigardeau, MO (US)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 10/239,092

(22) PCT Filed: Mar. 23, 2001

(86) PCT No.: PCT/JP01/02334

§ 371 (c)(1),
(2), (4) Date: Sep. 19, 2002

(87) PCT Pub. No.: WO01/71021

PCT Pub. Date: Sep. 27, 2001

(65) Prior Publication Data

US 2003/0059904 A1    Mar. 27, 2003

(30) Foreign Application Priority Data

Mar. 24, 2000  (JP) .............................. 2000-083648

(51) Int. Cl.
*C12P 13/04* (2006.01)
*C12N 9/10* (2006.01)
*C12N 1/20* (2006.01)
*C12N 15/00* (2006.01)
*C07H 21/04* (2006.01)

(52) U.S. Cl. ...................... 435/106; 435/183; 435/193; 435/252.33; 435/320.1; 536/23.2

(58) Field of Classification Search ................ 435/106, 435/183, 193, 252.33, 320.1; 536/23.2
See application file for complete search history.

(56) References Cited

FOREIGN PATENT DOCUMENTS

| EP | 0 356 739 | 3/1990 |
|---|---|---|
| EP | 0 436 886 | 7/1991 |
| EP | 0 694 614 | 1/1996 |
| EP | 0 745 679 | 12/1996 |
| EP | 0913466 A2 * | 5/1999 |
| WO | WO 87/02984 | 5/1987 |

OTHER PUBLICATIONS

Whalen et al. J Bacteriol. May 1982;150(2):739-46.*
Leyval et al. J Biotechnol. Sep. 4, 2003;104(1-3):241-52.*
Wang, et al., "Cloning and Characterization of the *Escherichia coli* K-12 Alanine-Valine Transaminase (avtA) Gene", Journal of Bacteriology vol. 169, No. 9 (1987), pp. 4228-4234.
Whalen, et al., "Analysis of an avtA::Mu d1 (AP lac) Mutant: Metabolic Role of Transaminase C", Journal of Bacteriology, vol. 150, No. 2 (1982), pp. 739-746.

* cited by examiner

*Primary Examiner*—Tekchand Saidha
*Assistant Examiner*—Christian L. Fronda
(74) *Attorney, Agent, or Firm*—Fitzpatrick, Cella, Harper & Scinto

(57) ABSTRACT

According to the present invention, by using a microorganism having the ability to produce the L-amino acid which carries the avtA gene encoding alanine-valine transaminase (transaminase C) and whose alanine-valine transaminase activity is enhanced compared with its parent strain, it is possible to reduce the production of by-product amino acids which disturb purification in L-amino acid production by fermentation, and an industrially advantageous process for producing an L-amino acid can be provided.

6 Claims, 1 Drawing Sheet

SEQUENCE LISTING

<160> NUMBER OF SEQ ID NOS: 2

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 1
tcgactgtct ggcgcagatg gatacgacct                                    30

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 2
cctgataagc gtagcgcatc aggcaatttt                                    30

PROCESS FOR PRODUCING L-AMINO ACIDS VIA FERMENTATION METHOD

TECHNICAL FIELD

The present invention relates to a process for producing L-amino acids by fermentation. Branched chain amino acids such as L-leucine and L-isoleucine are used as food products, feed additives, materials for the synthesis of drugs and agricultural chemicals, etc.

BACKGROUND ART

As the methods for production of L-amino acids by direct fermentation, some methods are known for producing L-leucine by using microorganisms belonging to the genus *Escherichia*, *Serratia*, *Corynebacterium* or *Arthrobacter*. Known methods for producing L-leucine by the use of microorganisms belonging to the genus *Escherichia* include: a method using a microorganism which is resistant to β-2-thienylalanine (Japanese Published Unexamined Patent Application No. 72695/81); a method using a microorganism which is resistant to L-ethionine (Japanese Published Unexamined Patent Application No. 55194/84); a method using a microorganism which is resistant to 2-ketobutyric acid (Japanese Published Unexamined Patent Application No. 9982/96); and a method using a microorganism which is resistant to 4-azaleucine or 5,5,5-trifluoroleucine (Japanese Published Unexamined Patent Application No. 70879/96).

Likewise, there are known methods for producing L-isoleucine by using microorganisms belonging to the genus *Escherichia*, *Serratia*, *Corynebacterium* or *Arthrobacter*. Known methods for producing L-isoleucine by the use of microorganisms belonging to the genus *Escherichia* include: a method using a microorganism which is resistant to thiaisoleucine, isoleucine hydroxamate, arginine hydroxamate, DL-ethionine, etc. (Japanese Published Unexamined Patent Application No. 130882/93); a method using a microorganism which is resistant to 2-ketobutyric acid (Japanese Published Unexamined Patent Application No. 9982/96); and a method using a microorganism which grows rapidly in a medium containing L-homoserine as the only nitrogen source (Japanese Published Unexamined Patent Application No. 322583/96).

However, these methods have the problem that L-amino acids other than the desired L-amino acids are formed as by-products in considerable amounts. Particularly, formation of L-valine in the process of producing L-leucine or L-isoleucine causes the rise in production cost or the lowering of purification yield and product purity because separation and removal of L-valine in the purification step is not easy.

Alanine-valine transaminase (transaminase C) is an enzyme which catalyzes the reversible coupled transamination reaction between L-alanine and pyruvic acid, and 2-oxoisovaleric acid and L-valine, as shown below.

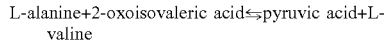
L-alanine+2-oxoisovaleric acid⇌pyruvic acid+L-valine

This enzyme is also known to catalyze the reversible coupled transamination reaction between L-alanine and pyruvic acid, and 2-oxobutyric acid and 2-aminobutyric acid, as shown below.

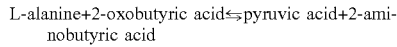
L-alanine+2-oxobutyric acid⇌pyruvic acid+2-aminobutyric acid

The gene encoding alanine-valine transaminase has been found in microorganisms such as *Escherichia coli* and *Salmonella typhimurium*. As for alanine-valine transaminase derived from *Escherichia coli*, there have been reports on the cloning of the gene encoding the enzyme (avtA) and the nucleotide sequence of the gene [J. Bacteriol., 169, 4228 (1987); Gene, 65, 195 (1988); Science, 277, 1453 (1997); Genbank, Accession No. AE00434 (1998)]. It is also reported that alanine-valine transaminase activity is enhanced by amplification of the avtA gene [J. Bacteriol. 169, 5610 (1987)].

The following have been reported on the physiological role of alanine-valine transaminase.

*Escherichia coli* which is deficient in ilvE encoding branched chain amino acid transaminase (transaminase B) exhibits the complete requirement for L-isoleucine, but not for L-valine (the leaky phenotype), indicating that alanine-valine transaminase is concerned in the conversion of 2-oxoisobutyric acid into L-valine as the second transaminase substituting for branched chain amino acid transaminase [*Escherichia coli* and *Salmonella typhimurium*, American Society for Microbiology, Washington, D. C. (1987)]. Further, the partial requirement for L-valine (the leaky phenotype) of the above mutant is complemented by amplifying the avtA gene [*Escherichia coli* and *Salmonella typhimurium*, American Society for Microbiology, Washington, D. C. (1987)].

However, there has been no report that the formation of L-valine can be reduced by enhancing the activity of alanine-valine transaminase.

DISCLOSURE OF THE INVENTION

An object of the present invention is to provide an efficient and industrially advantageous fermentative process for producing L-amino acids by reducing the formation of other amino acids as by-products.

The present inventors made intensive studies with the aim of reducing the formation of undesired amino acids as by-products in the production of an L-amino acid by fermentation. As a result, they discovered that the formation of undesired amino acids can be reduced by enhancing the activity of alanine-valine transaminase of a strain producing the desired L-amino acid, and have completed the invention.

The present invention relates to the following (1) to (11).

(1) A process for producing an L-amino acid which comprises culturing in a medium a microorganism having the ability to produce the L-amino acid whose alanine-valine transaminase activity is enhanced compared with its parent strain, allowing the L-amino acid to form and accumulate in the culture, and recovering the L-amino acid from the culture.

(2) The process according to (1), wherein the microorganism is selected from the group consisting of a mutant, a fused cell line, a transductant and a recombinant strain constructed by recombinant DNA technology.

(3) The process according to any of (1) or (2), wherein the microorganism is selected from the group consisting of the genera *Escherichia*, *Serratia*, *Corynebacterium* and *Arthrobacter*.

(4) The process according to (1) to (3), wherein the microorganism is *Escherichia coli* H-8719/pAD27 (FERM BP-7063) or *Escherichia coli* H-9156/pAD27.

(5) The process according to (1), wherein the L-amino acid is selected from the group consisting of L-leucine and L-isoleucine.

(6). The process according to (1), wherein the alanine-valine transaminase activity of the microorganism is enhanced by increasing the expression level of the alanine-valine transaminase gene in the cells of the microorganism.

(7) The process according to (1), wherein the alanine-valine transaminase activity of the microorganism is enhanced by increasing the copy number of the alanine-valine transaminase gene in the cells of the microorganism.

(8) A microorganism having the ability to produce an L-amino acid whose alanine-valine transaminase activity is enhanced compared with its parent strain.

(9) The microorganism according to (8), which is selected from the group consisting of a mutant, a fused cell line, a transductant and a recombinant strain constructed by recombinant DNA technology.

(10) The microorganism according to (8) or (9), which is selected from the group consisting of the genera *Escherichia*, *Serratia*, *Corynebacterium* and *Arthrobacter*.

(11) The microorganism according to any of (8) to (10), which is *Escherichia coli* H-8719/pAD27 (FERM BP-7063) or *Escherichia coli* H-9156/pAD27.

The present invention is described in detail below.

In the present invention, any microorganism can be employed so long as its alanine-valine transaminase activity is enhanced compared with its parent strain and it has the ability to produce an L-amino acid. The term "parent strain" as used herein means a microorganism used as a starting microorganism to construct a mutant, a fused cell line, a transductant or a recombinant strain. The microorganism whose alanine-valine transaminase activity is enhanced compared with its parent strain may be any of the mutant, the fused cell line, the transductant and the recombinant strain. Examples of the microorganisms include those selected from microorganisms belonging to the genera *Escherichia*, *Serratia*, *Corynebacterium* and *Arthrobacter*. Preferred examples are so-called coryneform glutamic acid-producing strains such as *Corynebacterium glutamicum* and *Corynebacterium lactofermentum,* and *Escherichia coli,* which are used in amino acid fermentation.

Specific examples of the parent strains are *Escherichia coli* H-8719 (an L-leucine-producing strain which is resistant to 4-azaleucine induced from FERM- BP-4704 strain) having the ability to produce L-leucine and *Escherichia coli* H-9156 (FERM BP-5056) having the ability to produce L-isoleucine.

The alanine-valine transaminase activity of these microorganisms can be enhanced, for example, by the following methods.

I. A method in which a mutant having an enhanced alanine-valine transaminase activity is selected from microorganisms obtained by treating a microorganism carrying the alanine-valine transaminase gene with a mutagen.

II. A method in which a mutation is introduced into the alanine-valine transaminase gene in vitro, and a gene encoding alanine-valine transaminase whose activity is higher than before the mutation introduction is selected from the mutated genes, and the selected gene is introduced into a host microorganism.

III. A method in which the copy number of the gene encoding alanine-valine transaminase in the cells is increased.

IV. A method in which the region responsible for the expression of the gene encoding alanine-valine transaminase is modified in vitro to increase the expression level of the gene, and the modified gene is substituted for the gene encoding alanine-valine transaminase on the host chromosome.

The above method in which a mutant having an enhanced alanine-valine transaminase activity is selected from microorganisms obtained by treating a microorganism carrying the alanine-valine transaminase gene with a mutagen can be carried out, for example, in the following manner. A microorganism carrying the alanine-valine transaminase gene is mutagenized by a known method using a mutagen such as N-methyl-N'-nitro-N-nitrosoguanidine, and a microorganism having enhanced alanine-valine transaminase activity compared with its parent strain subjected to mutagenesis is selected from the mutagen-treated microorganisms. The alanine-valine transaminase activity of a microorganism can be measured, for example, by culturing the microorganism in an appropriate medium, subjecting the cultured cells to centrifugation, disrupting the obtained cells according to a known method to prepare a crude enzyme solution, carrying out an enzymatic reaction using the crude enzyme solution and, as a substrate, L-alanine or pyruvic acid and L-valine, and measuring the amount of L-valine or L-alinine formed by the enzymatic reaction.

Examples of the methods in which a mutation is introduced into the alanine-valine transaminase gene in vitro and a gene encoding alanine-valine transaminase whose activity is higher than that before the mutation introduction is selected from the mutated genes include the following:

1) a method in which a deletion, substitution or addition of a base is introduced into the alanine-valine transaminase gene by site-specific mutagenesis [Nucleic Acids Research, 10, 6487 (1982); Proc. Natl. Acad. Sci., USA, 79, 6409 (1982); Proc. Natl. Acad. Sci., USA, 81, 5662 (1984); Science, 224, 1431 (1984); PCT WO85/00817 (1985); Nature, 316, 601 (1985); Gene, 34, 315 (1985); Nucleic Acids Research, 13, 4431 (1985); Current Protocols in Molecular Biology, John Wiley & Sons (1987–1997)] to obtain a gene encoding alanine-valine transaminase whose activity is higher than that before the mutagenesis; and 2) a method in which a mutation such as base substitution is introduced at random into the alanine-valine transaminase gene by error-prone polymerase chain reaction [Bio/Technol., 9, 1073 (1991) (hereinafter polymerase chain reaction is referred to as PCR)], and a gene encoding alanine-valine transaminase whose activity is higher than that before the mutagenesis is selected from the mutated genes.

The copy number of the gene encoding alanine-valine transaminase can be increased, for example, by cloning the gene encoding alanine-valine transaminase, and then, 1) ligating a DNA fragment comprising the gene encoding alanine-valine transaminase to a plasmid vector capable of autonomous replication in the cells of the desired microorganism, and introducing the resulting plasmid into the microorganism; or 2) integrating a recombinant DNA comprising the gene encoding alanine-valine transaminase into the chromosome of a strain to be used as the host by homologous recombination, or by using phage or transposon.

Examples of the methods in which the region responsible for the expression of the gene encoding alanine-valine transaminase is modified in vitro to increase the expression level of the gene and the modified gene is substituted for the gene encoding alanine-valine transaminase on the host chromosome include the following:

1) a method in which the region responsible for the expression of the gene is substituted by a known promoter having a strong promoter activity in a microorganism to be used as a host for introduction and expression of the gene; and 2) a method in which a deletion, substitution or addition of a base is introduced into DNA having a nucleotide sequence responsible for the expression of the gene by the above-described site-specific mutagenesis or error-prone PCR, and DNA increasing the expression level of the gene encoding alanine-valine transaminase compared with that before mutagenesis is selected from the mutated DNAs.

The gene encoding alanine-valine transaminase useful in the present invention may be derived from any cells, preferably a microorganism, more preferably a microorganism belonging to the genus *Escherichia* or *Salmonella*.

The gene encoding alanine-valine transaminase can be obtained, for example, by the following methods.

I. When the nucleotide sequence of the gene encoding alanine-valine transaminase of a microorganism is known, as is the case with *Escherichia coli* or *Salmonella typhimurium*, the gene can be obtained by PCR based on the nucleotide sequence using the chromosomal DNA of the microorganism as a template [PCR Protocols, Academic Press (1990)].

II. When the nucleotide sequence of the gene encoding alanine-valine transaminase of the cells having alanine-valine transaminase activity is not known, a cDNA library or a chromosomal DNA library derived from the cells is prepared according to a conventional method [Molecular Cloning, A Laboratory Manual, Second Edition (1989) (hereinafter abbreviated as Molecular Cloning, 2nd ed.)], and then, 1) the alanine-valine transaminase activity of each of the cells constituting the library is measured, and a cell comprising the gene encoding alanine-valine transaminase is selected from the cells, or 2) a cell comprising the gene encoding alanine-valine transaminase is selected from the cells constituting the library by colony hybridization or plaque hybridization (Molecular Cloning, 2nd ed.) using, as a probe, the alanine-valine transaminase gene of *Escherichia coli* or *Salmonella typhimurium*.

III. When the complete nucleotide sequence of the chromosomal DNA is known but the gene encoding alanine-valine transaminase is not specified, the gene having a nucleotide sequence highly homologous to the nucleotide sequence of the alanine-valine transaminase gene derived from *Escherichia coli* or *Salmonella typhimurium* is specified in the above complete nucleotide sequence by the use of an analysis software such as BLAST [J. Mol. Biol., 215, 403 (1990)] or FASTA [Methods in Enzymology, 183, 63 (1990)], and the desired gene is obtained by PCR.

Cloning of the avtA gene, which is the gene encoding alanine-valine transaminase of *Escherichia coli*, can be carried out, for example, in the following manner.

First, a region (ca. 1.9 kb) containing the avtA gene and its promoter sequence is amplified by PCR using, as a primer set, two kinds of primer DNAs designed and synthesized based on the sequence of the avtA gene derived from a microorganism belonging to the genus *Escherichia* and its neighboring sequence [Genbank, Accession No. AE00434 (1998)], for example, DNAs respectively having the nucleotide sequences shown in SEQ ID NOs: 1 and 2, and utilizing the chromosomal DNA of the microorganism as a template.

The obtained avtA gene is ligated to a plasmid vector capable of autonomous replication in the cells of a microorganism into which the gene is introduced, and the recombinant vector is introduced into the cells of the microorganism by a conventional method, whereby the avtA gene can be cloned.

Any plasmid capable of autonomous replication in the cells of a microorganism into which the gene encoding alanine-valine transaminase is introduced can be employed as the plasmid vector in the present invention. When the microorganism into which the gene is introduced is *Escherichia coli*, any plasmid capable of autonomous replication in the cells of *Escherichia coli* can be employed. Suitable plasmids include ZAP Express [Stratagene; Strategies, 5, 58 (1992)], pBluescript II SK(+) [Nucleic Acids Research, 17, 9494 (1989)], λzap II (Stratagene), λgt10, λgt11 [DNA Cloning, A Practical Approach, 1, 49 (1985)], λTriplEx (Clontech Laboratories, Inc.), λBlueMid (Clontech Laboratories, Inc.), λExCell (Pharmacia), pT7T318U (Pharmacia), pcD2 [Mol. Cell. Biol., 3, 280 (1983)], pUC18 [Gene, 33, 103 (1985)], pUC19 [Gene, 33, 103 (1985)] and their derivatives.

It is possible to increase the expression level of the gene encoding alanine-valine transaminase by using DNA prepared by ligating the avtA gene at a position downstream of a promoter which functions in the cells of a microorganism into which the gene is introduced. When the microorganism into which the gene is introduced is *Escherichia coli*, any promoter capable of functioning in the host cells may be employed. Suitable promoters include those derived from *Escherichia coli*, phage, etc. such as trp promoter ($P_{trp}$), lac promoter, $P_L$ promoter, $P_R$ promoter and T7 promoter. Artificially designed and modified promoters such as a promoter in which two $P_{trp}$s are combined in tandem ($P_{trp} \times 2$), tac promoter, lacT7 promoter and letI promoter can also be employed.

It is preferred to use a plasmid in which the distance between the Shine-Dalgarno sequence (ribosome binding sequence) and the initiation codon is adjusted to an appropriate length (e.g., 6 to 18 bases).

Examples of the methods for introducing the plasmid into the cells of a microorganism into which the gene is introduced include electroporation which causes incorporation of DNA into the cells by applying electrical pulses of high voltage [Nucleic Acids Res., 16, 6127 (1988)] and the protoplast method (Japanese Published Unexamined Patent Application No. 248394/88). When the plasmid is introduced into *Escherichia coli*, a method in which the permeability of DNA is increased using calcium chloride is also useful (Molecular Cloning, 2nd ed.).

The microorganism carrying the introduced plasmid comprising the gene encoding alanine-valine transaminase can be selected by using, as an indicator, the drug resistance of the microorganism acquired with the drug resistance gene on the plasmid. The transformant thus obtained can be identified to be the desired recombinant microorganism by examining its alanine-valine transaminase activity, the restriction enzyme map of the DNA fragment inserted into the plasmid or the nucleotide sequence thereof.

Production of an L-amino acid using the L-amino acid-producing strain thus obtained whose alanine-valine transaminase activity is enhanced compared with the host strain can be carried out by an ordinary culturing method used for production of L-amino acids by fermentation. That is, culturing is carried out in a medium containing carbon sources, nitrogen sources, inorganic salts, vitamins and other components necessary for the growth of the strain under aerobic conditions at appropriately adjusted temperature and pH.

Examples of the carbon sources include various carbohydrates such as glucose, fructose, sucrose and lactose, molasses containing them, cellulose hydrolyzate, crude sugar hydrolyzate and starch hydrolyzate.

Examples of the nitrogen sources include ammonia, ammonium salts of various inorganic or organic acids such as ammonium chloride, ammonium sulfate, ammonium acetate and ammonium phosphate, amines and other nitrogen-containing compounds, peptone, meat extract, yeast extract, corn steep liquor, casein hydrolyzate, soybean protein hydrolyzate, soybean cake hydrolyzate, and various fermented microbial cells and digested products thereof.

Examples of the inorganic salts include potassium dihydrogenphosphate, dipotassium hydrogenphosphate, magnesium phosphate, magnesium sulfate, sodium chloride, ferrous sulfate, manganese sulfate, copper sulfate and calcium carbonate.

Culturing is carried out under aerobic conditions, for example, by shaking culture or spinner culture under aeration. The culturing temperature is preferably 20 to 40° C. The pH of the medium is in the range of 5 to 9 and is preferably maintained at around neutrality. The pH adjustment is carried out by using calcium carbonate, an inorganic or organic acid, an alkali solution, ammonia, a pH buffer, etc. An L-amino acid is formed and accumulated in the culture usually by culturing for one to 7 days.

The L-amino acid can be recovered from the culture by known methods such as the ion exchange resin method, concentration, salting-out and precipitation [The Society of Chemical Engineers, Japan (ed.), Handbook of Bioseparation Process, Kyoritsu Shuppan (1996)].

Examples of the present invention are shown below. These examples are not to be construed as limiting the scope of the invention.

BEST MODES FOR CARRYING OUT THE INVENTION

EXAMPLE 1

Figure 1:
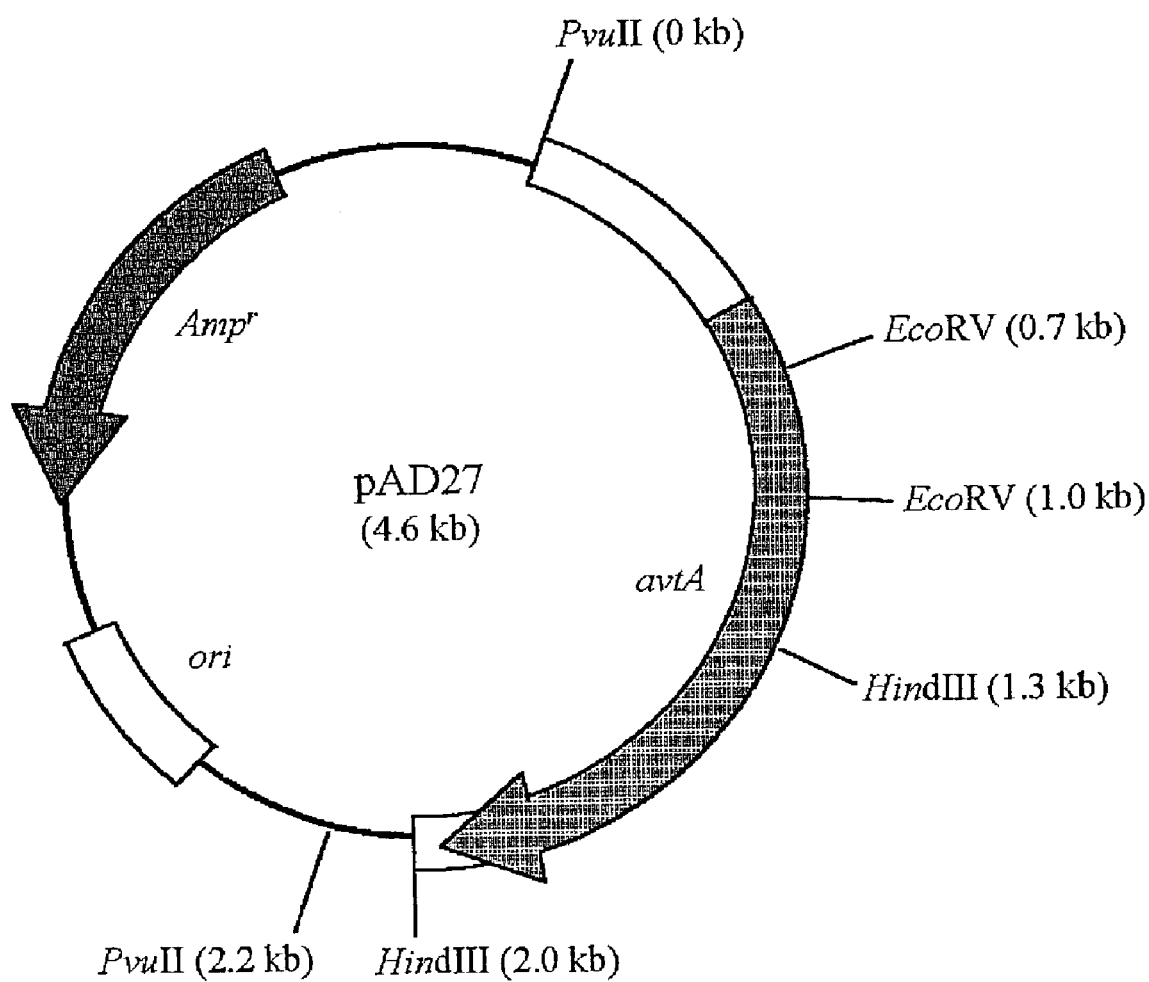
FIG. 1 shows the structure of plasmid pAD27.
The symbols used in FIG. 1 represent the following.
Amp$^r$: Ampicillin resistance gene
ori: Replication origin functioning in *Escherichia coli*
avtA: Gene encoding alanine-valine transaminase derived from *Escherichia coli*

Cloning of the AvtA Gene of *Escherichia coli*

W3110 strain (ATCC 27325) derived from *Escherichia coli* K-12 was spread on LB agar plate medium [10 g/l tryptone peptone (Difco Laboratories Inc.), 5 g/l yeast extract, 10 g/l sodium chloride and 15 g/l agar, pH 7.5], followed by culturing at 37° C. for 24 hours. One platinum loop of the cultured cells was inoculated into 8 ml of LB medium [10 g/l tryptone peptone (Difco Laboratories Inc.), 5 g/l yeast extract and 10 g/l sodium chloride, pH 7.5], followed by shaking culture (oscillatory shaking: 300 rpm) in a large test tube (diameter: 25 mm, length: 200 mm) at 37° C. for 24 hours. The resulting culture (1.25 ml) was transferred into 250 ml of LB medium and cultured with shaking (rotary shaking: 200 rpm) in a 2-L Erlenmeyer flask at 37° C. for 24 hours.

The obtained culture was centrifuged at 5,000 rpm at 4° C. for 10 minutes and the cells were collected. The cells were washed with TE buffer [10 mmol/l tris(hydroxymethyl)aminomethane, 1 mmol/l disodium ethylenediaminetriacetate, pH 7.5] and then collected. The chromosomal DNA was isolated from the collected cells according to the method of Saito-Miura [Biochem. Biophys. Acta, 72, 619 (1963)].

In order to amplify the avtA gene using the chromosomal DNA as a template by PCR, oligonucleotide primers respectively having the nucleotide sequences shown in SEQ ID NOs: 1 and 2 were synthesized on the basis of the known nucleotide sequences of the avtA gene and its vicinities [Genbank, Accession No. AE00434 (1998)]. The DNAs having the nucleotide sequences shown in SEQ ID NOs: 1 and 2 are primers comprising sequences homologous or complementary to a sequence upstream of the avtA gene comprising the promoter and a sequence downstream of the avtA gene, respectively.

The avtA gene was amplified by PCR using the above-described chromosomal DNA and primer set. PCR was carried out by repeating 30 times a reaction cycle in which reaction is conducted at 94° C. for one minute, at 55° C. for two minutes and at 72° C. for two minutes.

The DNA fragment (1.9 kb) amplified by PCR was blunted with T4 DNA polymerase and then ligated to plasmid vector pUC19 cleaved with restriction enzymes EcoRI and PstI and blunted with T4 DNA polymerase using T4 DNA ligase. This reaction product was used for transformation of *Escherichia coli* H-8719 by electroporation. The resulting cell suspension was spread on LB agar plate medium containing 100 mg/l ampicillin, followed by culturing at 37° C. for 24 hours. The colonies which grew on the agar plate medium were selected, and the structure of the DNA fragments inserted into the plasmids carried by these transformants was analyzed with various restriction enzymes, whereby it was confirmed that the avtA gene existed on the inserted DNA fragments.

The alanine-valine transaminase activity of these transformants was measured in the following manner. After shaking culture (oscillatory shaking: 300 rpm) in LB medium at 30° C. for 24 hours, the cultured cells were washed by suspension and centrifugation twice with an aqueous solution of 8.5 g/l sodium chloride and once with buffer A (25 mmol/l potassium phosphate buffer, pH 7.0, 50 ml/l glycerin, 0.1 mmol/l trisodium ethylenediaminetetraacetate, 0.2 mmol/l dithiothreitol and 0.2 mmol/l pyridoxal phosphate). The cells were then resuspended in the same buffer at a density of 100 g wet cell weight per liter. The suspended cells were disrupted by sonication, followed by centrifugation to prepare a crude enzyme solution. The obtained crude enzyme solution (20 μl) was added to 980 μl of a reaction solution prepared by adding 10 mmol/l pyruvic acid and 10 mmol/l L-valine to buffer A, followed by reaction at 37° C. for 30 minutes. The formed L-alanine was determined by high performance liquid chromatography (HPLC) to measure the alanine-valine transaminase activity. The conditions for HPLC analysis are as follows.
Column: YMC ODS-AQ312 column
Mobile phase: 2.94 g/l trisodium citrate, 1.42 g/l sodium sulfate, 63 ml/l n-propanol, 3 g/l sodium dodecyl sulfate, pH 3.75 (adjusted with 2 mol/l sulfuric acid)
Mobile phase flow rate: 2 ml/minute
Reaction solution: 18.5 g/l boric acid, 11 g/l sodium hydroxide, 3 ml/l Brig-35, 0.6 g/l o-phthalaldehyde, 2 ml/l mercaptoethanol
Reaction solution flow rate: 1 ml/minute
Fluorescence detection: excitation wavelength 345 nm detection wavelength 455 nm As a result, it was found that the alanine-valine transaminase activity of the transformant was more than 10 times higher than that of *Escherichia coli* H-8719 regarded as 1. The plasmid thus obtained was named pAD27 (FIG. 1).

The recombinant *Escherichia coli* H-8719/pAD27 obtained as above was deposited with the National Institute of Bioscience and Human-Technology, National Institute of Advanced Industrial Science and Technology, Ministry of Economy, Trade and Industry, 1–3, Higashi 1-chome, Tsukuba-shi, Ibaraki, 305–0046 Japan, on March 2, 2000 with accession number FERM BP-7063 under the Budapest Treaty.

Plasmid pAD27 was prepared from cultured cells of *Escherichia coli* H-8719/pAD27, and *Escherichia coli* H-9156 having L-isoleucine productivity was transformed using the obtained plasmid by electroporation.

Recombinant *Escherichia coli* H-9156/pAD27 carrying pAD27 was obtained by selecting an ampicillin-resistant transformant in the same manner as described above. The alanine-valine transaminase activity of the transformant thus obtained was measured in the same manner as described above. As a result, it was confirmed that the alanine-valine-transaminase activity of the transformant was more than 10 times higher than that of *Escherichia coli* H-9156 regarded as 1.

EXAMPLE 2

L-Leucine Production Test

L-Leucine production test on *Escherichia coli* H-8719, H-8719/pAD27 carrying plasmid pAD27 comprising the avtA gene, and H-8719/pUC19 carrying plasmid vector pUC19 was carried out in the following manner.

H-8719/pAD27 and H-8719/pUC19 were separately spread on LB agar plate medium containing 100 mg/l ampicillin, and H-8719 was spread on LB agar plate medium containing no ampicillin. Each of the strains was cultured at 30° C. for 24 hours. One platinum loop of the cultured cells was inoculated into 6 ml of a seed medium (20 g/l glucose, 10 g/l peptone, 10 g/l yeast extract, 2.5 g/l sodium chloride and 10 g/l calcium carbonate, pH 7.4), followed by shaking culture (oscillatory shaking: 300 rpm) in a large test tube (diameter: 25 mm, length: 200 mm) at 30° C. for 17 hours. The obtained culture (0.1 ml) was transferred into 6 ml of a production medium (65 g/l glucose, 2 g/l corn steep liquor, 16 g/l ammonium sulfate, 2 g/l potassium dihydrogenphosphate, 40 g/l magnesium phosphate and 10 g/l calcium carbonate, pH 7.0), followed by shaking culture (oscillatory shaking: 300 rpm) in a large test tube (diameter: 25 mm, length: 200 mm) at 30° C. for 48 hours.

After the completion of culturing, the amounts of L-leucine formed and accumulated in the culture and L-valine formed as a by-product were determined by HPLC (the same method as that for the determination of L-alanine described in Example 1).

The above-described culturing test was carried out 20 times independently, and the average values of the obtained results are shown in Table 1.

TABLE 1

| Strain | Leu [g/l] | Val [g/l] | Val/Leu [%] |
|---|---|---|---|
| H-8719 | 12.1 | 0.17 | 1.40 |
| H-8719/pUC19 | 12.4 | 0.18 | 1.44 |
| H-8719/pAD27 | 12.6 | 0.08 | 0.65 |

Average values (n = 20)

The three strains showed almost equal productivity of L-leucine. The ratio of L-valine as a by-product to L-leucine with H-8719/pAD27 in which the expression level of the avtA gene increased was reduced compared with that with the host H-8719 constantly, and the reduction rate was about 54%.

The above results indicate that the formation of L-valine as a by-product which disturbs purification in L-leucine production by fermentation can be significantly reduced by enhancing the activity of alanine-valine transaminase encoded by the avtA gene of an L-leucine-producing strain.

EXAMPLE 3

L-Isoleucine Production Test

L-Isoleucine production test on *Escherichia coli* H-9156, H-9156/pAD27 carrying plasmid pAD27 comprising the avtA gene, and H-9156/pUC19 carrying plasmid vector pUC19 was carried out in the following manner.

H-9156/pAD27 and H-9156/pUC19 were separately spread on LB agar plate medium containing 100 mg/l ampicillin, and H-9156 was spread on LB agar plate medium containing no ampicillin. Each of the strains was cultured at 30° C. for 24 hours. One platinum loop of the cultured cells was inoculated into 6 ml of a seed medium (20 g/l glucose, 10 g/l peptone, 10 g/l yeast extract, 2.5 g/l sodium chloride and 10 g/l calcium carbonate, pH 7.4), followed by shaking culture (oscillatory shaking: 300 rpm) in a large test tube (diameter: 25 mm, length: 200 mm) at 30° C. for 17 hours. The obtained culture (0.1 ml) was transferred into 6 ml of a production medium (65 g/l glucose, 2 g/l corn steep liquor, 16 g/l ammonium sulfate, 2 g/l potassium dihydrogenphosphate, 0.1 g/l DL-methionine, 40 g/l magnesium phosphate and 10 g/l calcium carbonate, pH 7.0), followed by shaking culture (oscillatory shaking: 300 rpm) in a large test tube (diameter: 25 mm, length: 200 mm) at 30° C. for 48 hours.

After the completion of culturing, the amounts of L-isoleucine formed and accumulated in the culture and L-valine formed as a by-product were determined by high performance liquid chromatography. The measurement conditions are the same as those described in Example 2.

The above-described culturing test was carried out 20 times independently, and the average values of the obtained results are shown in Table 2.

TABLE 2

| Strain | Ile [g/l] | Val [g/l] | Val/Ile [%] |
|---|---|---|---|
| H-9156 | 13.4 | 3.6 | 26.6 |
| H-9156/pUC19 | 13.4 | 3.4 | 25.7 |
| H-9156/pAD27 | 13.0 | 1.8 | 13.9 |

Average values (n = 20)

The three strains showed almost equal productivity of L-isoleucine. The ratio of L-valine as a by-product to L-isoleucine with H-9156/pAD27 in which the expression level of the avtA gene increased was reduced compared with that with the host H-9156 constantly, and the reduction rate was about 48%.

The above results indicate that the formation of L-valine as a by-product which disturbs purification in L-isoleucine production by fermentation can be significantly reduced by enhancing the activity of alanine-valine transaminase encoded by the avtA gene of an L-isoleucine-producing strain.

INDUSTRIAL APPLICABILITY

According to the present, by using a microorganism having the ability to produce the L-amino acid whose alanine-valine transaminase (transaminase C) activity is enhanced, it is possible to reduce the production of by-product amino acids which disturb purification in L-amino acid production by fermentation, and an industrially advantageous process for producing an L-amino acid can be provided.

Sequence Free Text

SEQ ID NO: 1—Description of the artificial sequence: Synthetic DNA

SEQ ID NO: 2—Description of the artificial sequence: Synthetic DNA

The invention claimed is:

1. A process for producing L-leucine or L-isoleucine which comprises:
   culturing in a medium a recombinant strain of a microorganism belonging to the genus *Escherichia, Serratia, Corynebacterium* or *Arthrobacter* which has the ability to produce L-leucine or L-isoleucine and whose alanine-valine transaminase activity is enhanced by increasing its copy number of *Escherichia coli* DNA encoding alanine-valine transaminase in the cells of the microorganism,
   allowing L-leucine or L-isoleucine to form and accumulate in the culture, and
   recovering L-leucine or L-isoleucine from the culture, wherein the ratio of a by-product L-valine: L-leucine or L-isoleucine of the recombinant microorganism is reduced, compared to that of an unmodified microorganism.

2. The process according to claim 1, wherein the microorganism is *Escherichia coli* H-8719/pAD27 (FERM BP-7063).

3. The process according to claim 1, wherein the microorganism is *Escherichia coli* H-9156/pAD27.

4. A recombinant strain of a microorganism belonging to the genus *Escherichia, Serratia, Corynebacterium* or *Arthrobacter* which has the ability to produce L-isoleucine and whose alanine-valine transaminase activity is enhanced by increasing its copy number of *Escherichia coli* DNA encoding alanine-valine transaminsae in the cells of the microorganism, wherein an unmodified parent strain of the recombinant strain has the ability to produce L-isoleucine and the ratio of a by-product L-valine: L-isoleucine of said recombinant strain is reduced, compared to that of said parent strain.

5. *Escherichia coli* H-8719/pAD27 (FERM BP-7063), whose alanine-valine transaminase activity is enhanced compared with its parent strain.

6. *Escherichia coli* H-9156/pAD27, whose alanine-valine transaminase activity is enhanced compared with its parent strain.

* * * * *

UNITED STATES PATENT AND TRADEMARK OFFICE
CERTIFICATE OF CORRECTION

| | |
|---|---|
| PATENT NO. | : 7,202,060 B2 |
| APPLICATION NO. | : 10/239092 |
| DATED | : April 10, 2007 |
| INVENTOR(S) | : Masato Ikeda et al. |

It is certified that error appears in the above-identified patent and that said Letters Patent is hereby corrected as shown below:

<u>ON COVER PAGE AT (75) INVENTORS</u>

"Jun-ichi Takano, Cape Gigardeau, MO (US)" should read --Jun-ichi Takano, Cape Girardeau, MO (US)--.

<u>COLUMN 4</u>

Line 11, "L-alinine" should read --L-alanine--.

<u>COLUMN 12</u>

Line 36, "transaminsae" should read --transaminase--.

Signed and Sealed this

Seventh Day of August, 2007

JON W. DUDAS
*Director of the United States Patent and Trademark Office*